United States Patent
Nelson et al.

(10) Patent No.: US 6,656,741 B1
(45) Date of Patent: Dec. 2, 2003

(54) AIR GAP FOR CONTROLLING SAMPLE ABSORPTION AND HEMATOCRIT DEPENDENCE

(75) Inventors: Eric M. Nelson, San Clemente, CA (US); Matthew A. Coe, La Mesa, CA (US)

(73) Assignee: Diabetes Diagnostics, Inc., San Diego, CA (US)

( * ) Notice: Subject to any disclaimer, the term of this patent is extended or adjusted under 35 U.S.C. 154(b) by 0 days.

(21) Appl. No.: 09/261,707

(22) Filed: Mar. 3, 1999

(51) Int. Cl.[7] .............................................. G01N 33/48
(52) U.S. Cl. ...................... 436/169; 436/177; 436/180; 436/63; 422/58; 422/61
(58) Field of Search .............................. 422/56, 58, 61; 436/63, 177, 179, 180, 169, 164, 174

(56) References Cited

U.S. PATENT DOCUMENTS

| | | | |
|---|---|---|---|
| 3,884,641 A | 5/1975 | Kraffczyk et al. ............. 23/253 |
| 3,992,158 A * | 11/1976 | Przybylowicz et al. ....... 422/58 |
| 4,065,263 A | 12/1977 | Woodbridge, III ........... 23/253 |
| 4,810,470 A * | 3/1989 | Burkhardt et al. ............ 422/58 |
| 4,965,047 A | 10/1990 | Hammond .................... 422/58 |
| 5,047,206 A | 9/1991 | Dombrowski ................ 422/56 |
| 5,104,811 A | 4/1992 | Berger et al. ............... 436/164 |
| 5,104,813 A * | 4/1992 | Besemer et al. .............. 422/58 |
| 5,275,785 A * | 1/1994 | May et al. ..................... 422/56 |
| 5,419,870 A * | 5/1995 | Parker ......................... 422/56 |
| 5,470,752 A | 11/1995 | Burd et al. .................... 436/87 |
| 5,597,532 A | 1/1997 | Connolly |
| 5,695,949 A | 12/1997 | Galen et al. |
| 5,712,170 A * | 1/1998 | Kouvonen et al. ............. 42/58 |
| 5,725,774 A | 3/1998 | Neyer ......................... 210/645 |
| 5,762,871 A | 6/1998 | Neyer ......................... 422/57 |
| 5,820,826 A | 10/1998 | Moorman ................... 422/104 |
| 6,024,919 A | 2/2000 | Nelson et al. |

FOREIGN PATENT DOCUMENTS

| | | |
|---|---|---|
| EP | 0215419 A | 3/1987 |
| WO | WO 00/52468 | 9/2000 |

OTHER PUBLICATIONS

PCT International Search Report, Appln. No. PCT/US00/05509, dated Jan. 8, 2000, which corresponds to this U.S. Appln. No. 09/261,707.

* cited by examiner

*Primary Examiner*—Lyle A. Alexander

(57) ABSTRACT

A method and apparatus for controlling the absorption of a liquid sample through an absorbent layer (2) and reducing the effect of hematocrit by applying the sample on one side of the layer (2a) and providing an air gap (4c) on the opposite side, so that absorption is controlled by preventing the release of air from the air gap.

7 Claims, 4 Drawing Sheets

# AIR GAP FOR CONTROLLING SAMPLE ABSORPTION AND HEMATOCRIT DEPENDENCE

BACKGROUND OF THE INVENTION

1. Field of the Invention

The present invention relates to analyzing liquid samples and more specifically to controlling the absorption of a liquid sample by an absorbent layer, thereby reducing the effect of hematocrit.

2. Background Information

Test strips are widely available for conveniently analyzing liquid samples. Typically, a test strip has one or more layers of absorbent material containing chemical reagents. When the liquid sample is applied to the absorbent layers, the reagents react with the components of interest in the test sample. The resulting reaction can then be measured by a variety of means to yield a measurement of the components in the sample.

For example, it is useful for certain diabetes patients to monitor the concentration of glucose in their blood. A glucose test strip can have an absorbent layer containing reagents that react with glucose present in the blood sample. When a patient applies a blood sample to the absorbent layer, the reagents then react with the glucose in the sample. If the reaction results in a detectable color change—turning the absorbent layer from colorless to dark blue, for example—the reaction can then be measured, and the amount of color produced related to the concentration of glucose in the blood sample.

A patient will typically use the test strip with a separate device that can measure the chemical reaction on the absorbent layer and display the patient's blood glucose concentration. One such device uses a reflectance meter, which measures reflected light of specific wavelengths, to monitor the light reflected from the surface of the absorbent layer. As the chemical reaction in the absorbent layer causes the color change, the reflectance meter can monitor the reaction by detecting changes in the light reflected from the surface of the absorbent layer. For example, as the chemical reaction proceeds, the reflectance meter can measure an increase of blue light reflected from the absorbent layer surface. Thus, the reflectance of light from the absorbent layer can be used to monitor the chemical reaction and thereby determine the glucose concentration in the blood sample.

However, these reflectance measurements can be subject to variability, leading to inconsistent results. One factor is the volume of liquid sample applied to the absorbent layer. Ideally, when the sample is applied to the absorbent layer, it should be thoroughly absorbed by the layer. In practice, however, excess sample may be applied so that the absorbent layer becomes overly saturated with the sample. As a result, a layer of excess sample can collect on the bottom surface of the absorbent layer, causing the surface to become shiny. This shininess, called wet-through, can dramatically increase the reflectance of the absorbent layer, distorting the measurement of the reaction and providing misleading information to the patient.

A second variable that can affect the test results is the hematocrit of the patient's blood, which is a measure of the relative amount of red blood cells and plasma in a blood sample. Because the hematocrit of a patient's blood sample can vary, the absorption of the sample by the absorbent layer can vary as well, resulting in hematocrit-dependent measurements of the patient's blood glucose concentration.

Thus, there is a need for controlling the absorption of a liquid sample by an absorbent layer and reducing the effect of hematocrit. The present invention satisfies these needs and provides related advantages as well.

SUMMARY OF THE INVENTION

The present invention provides a method for controlling the absorption of a liquid sample through an absorbent layer 2 by (a) providing an air gap 4c defined by the absorbent layer 2, at least one side wall 4d and a translucent window 6; and (b) applying the liquid sample to the absorbent layer on the side opposite to the air gap 2a. As a result, the sample absorption is controlled by preventing the release of air from the air gap 4c.

The present invention also provides an apparatus for performing the method of the invention. The apparatus has an absorbent layer 2, at least one side wall 4d and a translucent window 6, where the layer, walls and window define an air gap 4c.

Figure 1:
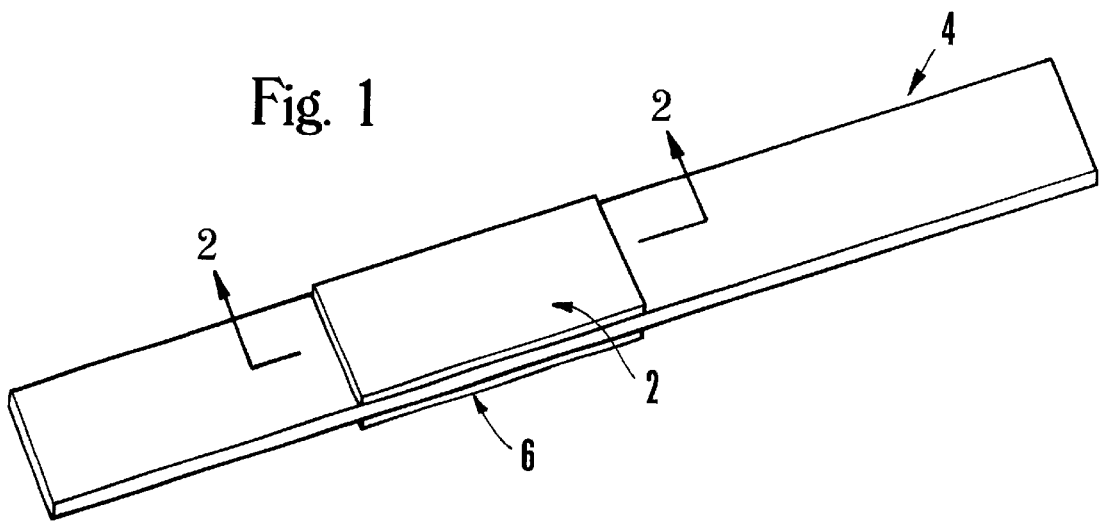
FIG. 1 shows an isometric view of one embodiment of the apparatus (not to scale).
Figure 2:
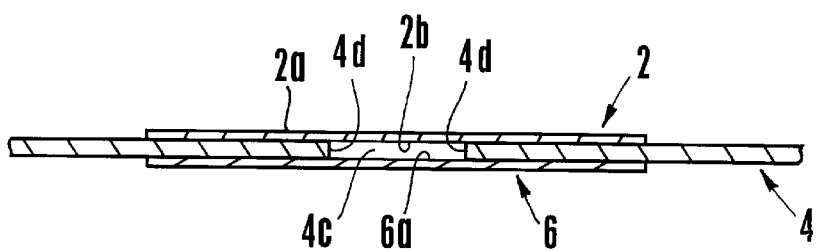
FIG. 2 shows a cross-sectional view of one embodiment of the apparatus (not to scale). The plane of the cross-section is indicated in FIG. 1.
Figure 3:
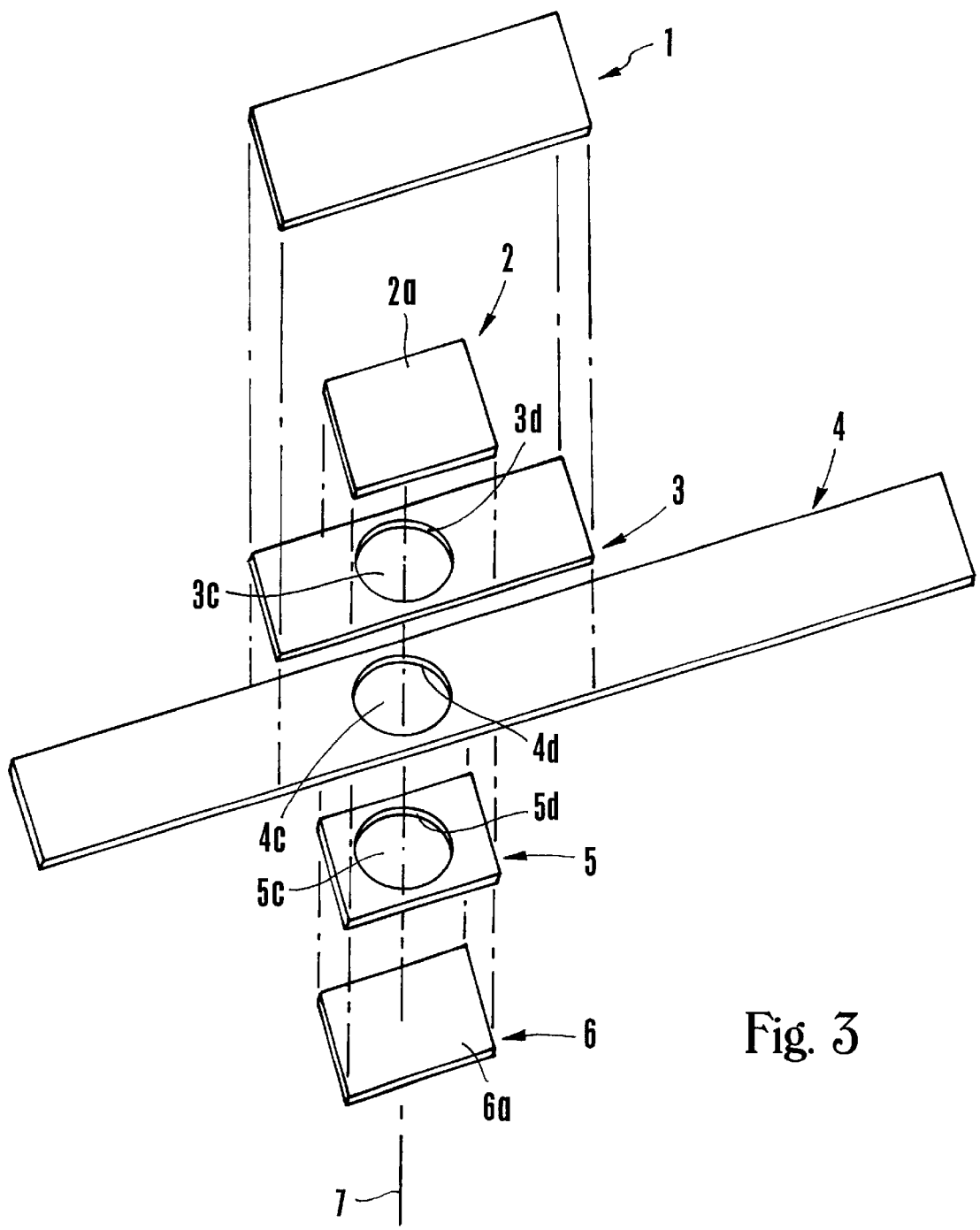
FIG. 3 shows an exploded isometric view of another embodiment of the apparatus including optional elements (not to scale).
Figure 4:
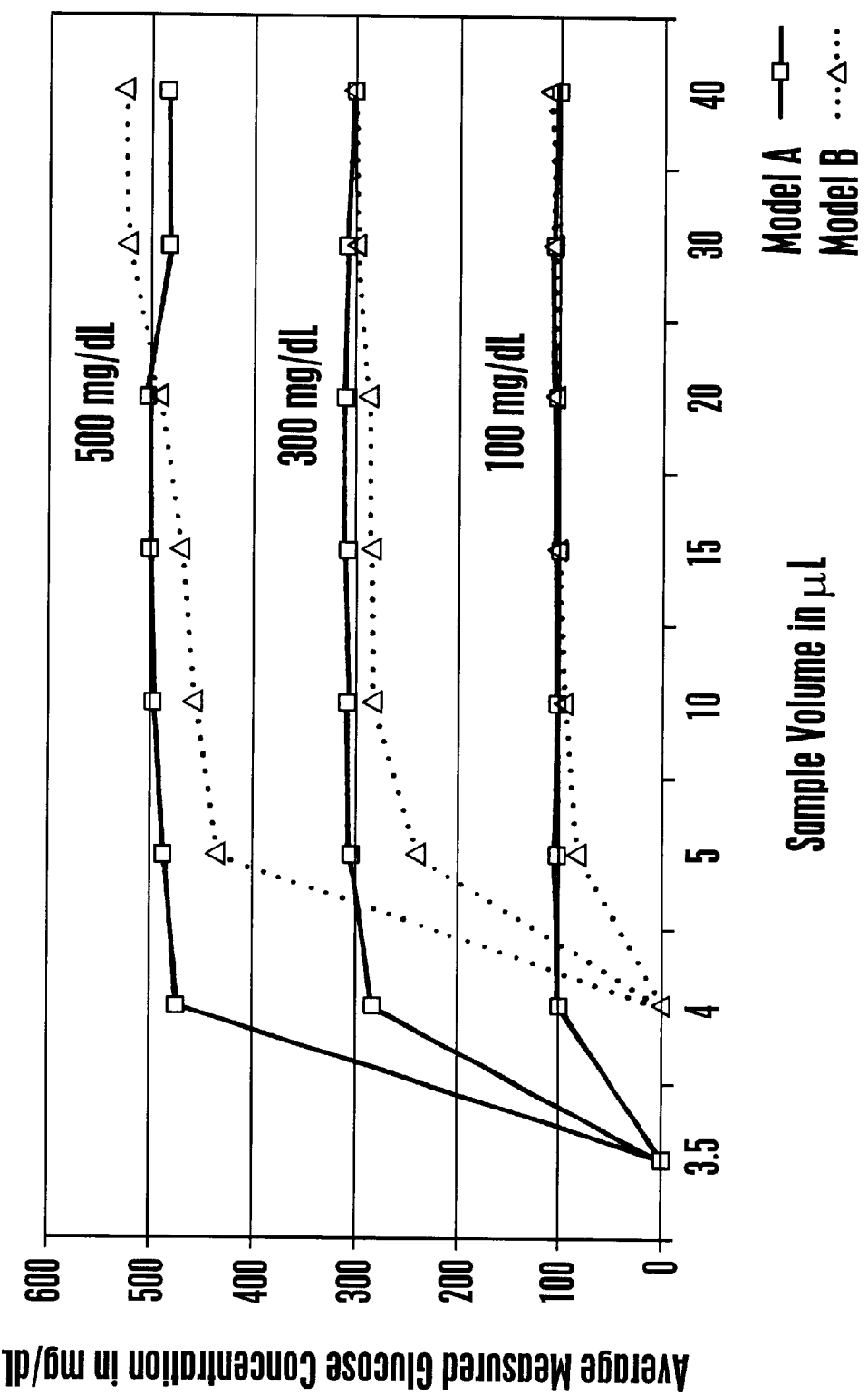

For convenience, the elements and features assigned numbers in FIGS. 1 to 3 are listed below:

1: Second layer (optional)
2: Absorbent layer, with application surface 2a and opposite viewing surface 2b.
3: Adhesive layer with hole 3c and inner surface 3d
4: Handle, with hole 4c and inner surface 4d
5: Adhesive layer with hole 5c and inner surface 5d
6: Translucent window with surface 6a.
7: Generalized line of sight FIG. 4 compares the relative volume-dependence of test strip Model A (with air gap) and Model B (without air gap).

Figure 5:
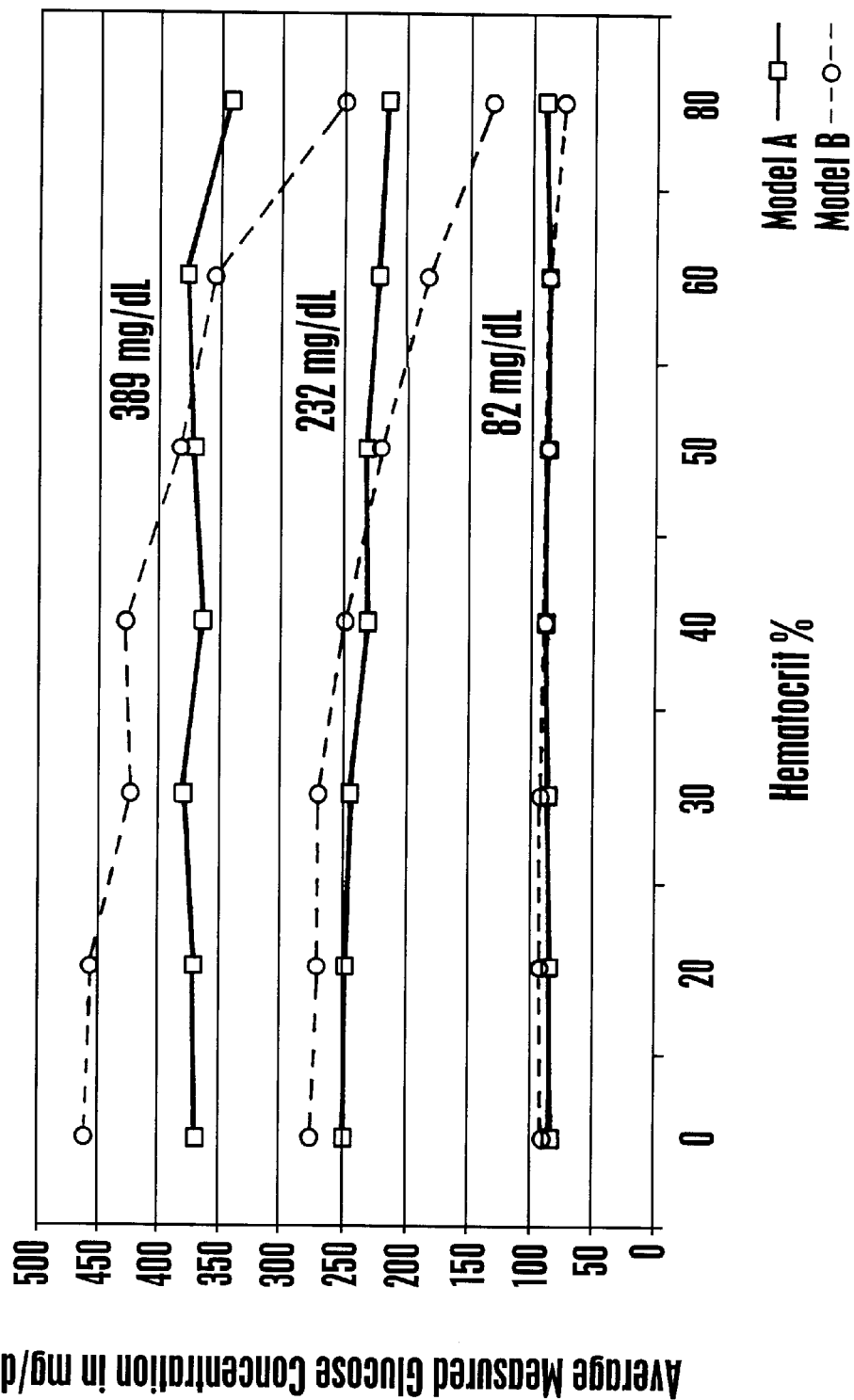

FIG. 5 compares the relative hematocrit-dependence of test strip Models A and B.

DETAILED DESCRIPTION OF THE INVENTION

The present invention provides a method and apparatus for controlling the absorption of a liquid sample by an absorbent layer. When a liquid sample is applied to the application surface 2a of the absorbent layer 2, the sample is absorbed. As shown in the embodiment of FIG. 2, an air gap 4c is provided, defined by the viewing surface 2b on the opposite side of the absorbent layer 2, at least one side wall 4d and a surface of a translucent window 6a. The "air gap" thus defined is an air-tight chamber with ambient air pressure.

Absorption of the liquid sample causes a slight increase in pressure within the air gap compared with the ambient pressure. This pressure increase can be explained by the decrease in effective volume of the air gap as the liquid absorbed by the layer displaces air within the layer. Because the air gap lacks an exit for the displaced air to escape, the air gap effectively prevents further sample from being absorbed by the absorbent layer.

As a result of the air gap, excess sample is not absorbed by the absorbent layer, but may pool on the application surface 2a or be absorbed by an optional second layer 1. Otherwise, a layer of excess sample could form on the viewing surface of the absorbent layer 2b, an undesirable result called wet-through. Thus, absorption of excess liquid sample is controlled by providing an air gap. "Liquid samples" that can be used with the invention encompass any fluid containing an analyte to be measured, for example blood, serum or plasma. The term also encompasses other "human body fluids" such as sweat, tears, saliva, semen, cerebrospinal fluid, sputum, urine and cervical mucus or swabbings. The term further encompasses food, environmental or industrial samples, depending on the desired application of the article, as long as they are liquid and contain an analyte for measurement.

The liquid sample can be analyzed for specific "analytes" of interest, which are any substances to be detected or quantitated in terms of concentration. For example, the analyte can be glucose, fructose, or other sugars, cholesterol, ketones, lipids, uric acid or specific amino acids such as phenylalanine. The analyte can also be proteins, for example enzymes such as amylase, creatine kinase or alanine aminotransferase. Furthermore, the analyte can be glycated proteins, for example serum or plasma glycated protein as measured by fructosamine, or red blood cell glycated protein as measured by glycated hemoglobin, in particular $Hb_{A1C}$. Other analytes are described in U.S. Pat. No. 5,597,532, incorporated herein by reference.

The "absorbent layer" can be any material that is permeable to gas when dry and can absorb liquid, but is relatively less permeable to gas when saturated or partially saturated with liquid. A particular absorbent layer is BIODYNE A 0.65 µm pore size nylon membrane (Pall Corp.; East Hills, N.Y.). The absorbent layer can contain a reagent that indicates the presence of an analyte such as glucose or fructosamine. Representative absorbent layers are described in U.S. Pat. Nos. 5,470,752, U.S. Pat. No. 5,597,532 and U.S. Pat. No. 5,695,949, each incorporated herein by reference.

A particularly useful absorbent layer contains a reagent that reacts with glucose in the liquid sample, for example a glucose oxidase/horseradish peroxidase system (Toyobo Inc.; Tokyo, Japan). Another useful system for reacting with glucose is N-ethyl-N-2-hydroxy-3-sulfopropyl-3,5-dimethylaniline (MAOS) (Dojindo Laboratories; Kumamoto, Japan) and N-ethyl-N-(2-hydroxy-3-sulfopropyl)-m-toluidine (TOOS). Other reagents include the combination of 4-aminoantipyrene and chromotropic acid (AAP-CTA) and the combination of 3-methyl-2-benzothiazoline hydrazone hydrochloride (MBTH) and either 3-dimethylaminobenzoic acid (DMAB) or 8-anilo-1-napthalenesulfonate (ANS).

The absorbent layer can be attached to a handle 4 so the user to hold the test strip without touching the absorbent layer. The handle contains a hole 4c, whose inner walls 4d partially define the air gap. For example, FIG. 3 shows that the side wall 4d is the inner surface of a hole 4c. Although hole 4c is circular in FIG. 3, it can also be of any shape so that there can be two or more distinct side walls forming the air gap.

The handle 4 can be attached to the absorbent layer 2 by any means for adhering two layers together so long as the resulting air gap is secure against the escape of air and does not occlude the viewing surface of the absorbent layer 2b along the line of sight 7. For example, the means for adhering can be acrylic-, rubber- or silicone-based adhesives. A particularly useful acrylic-based adhesive layer is FAS-TAPE 8311 double-coated acrylic-based adhesive (Avery-Dennison, Inc.; Pasadena, Calif.). Other adhesives include 3M 444 or 3M 415 double-coated adhesives (3M; Minneapolis, Minn.). Means for adhering the sintered polymer to the solid can also include PVC plastic pipe cement, epoxy, heat staking, clamping, bolting, nailing, compression fitting and immobilization by vacuum.

The test strip also has a translucent window 6, which partially defines the air gap 4c by one of its surfaces 6a. The "translucent window" should allow light to travel substantially along line of sight 7 to pass through the window 6 and reach the viewing surface 2b and be reflected back through window 6 so that the reflected light can be detected.

Because the liquid sample may be warmer or colder than the ambient temperature moisture may form on a surface of the window 6, interfering with light along the line of sight. Accordingly, the window may be treated to be "non-fogging" so that temperature differences in the window do not result in condensation of moisture from the ambient atmosphere. The window 6 can be attached to the handle 4 by any of the means for adhering two layers discussed above.

Thus, as shown in FIG. 3, an adhesive layer 3 can be used to attach the absorbent layer 2 to the handle 4, and another adhesive layer 5 can be used to attach the handle 4 to the window 6. In such cases, the adhesive layers 3 and 5 should have holes 3c and 5c so that they do not interfere with line of sight 7. Furthermore, the air gap will then be defined by the viewing surface of the absorbent layer 2b, by the inner side walls of the adhesive layer 3d, of the handle 4d and of the second adhesive layer 5d, and by the surface of the window 6a.

Additional layers can be added to the apparatus, for example a second layer 1 for separating a whole blood sample and allowing blood plasma to reach the application surface of absorbent layer 2a. Such layers are well known in the art and are exemplified by the whole blood separation layers in U.S. Pat. No. 5,725,774, which is incorporated by reference.

EXAMPLES

I. Construction of Test Strip with Air Gap

To compare the performance of test strips with and without the air gap feature, three models of test strips were assembled: Model A with the air gap and Models B and C without an air gap. Each of the models had a solid polyester handle 4 and an absorbent layer 2, which was BIODYNE A 0.65 µm pore size nylon membrane (Pall Corp.; East Hills, N.Y.). The absorbent layer was impregnated with a glucose oxidase/horseradish peroxidase system (Toyobo Inc.; Tokyo, Japan) and MAOS (N-ethyl-N-2-hydroxy-3-sulfopropyl-3, 5-dimethylaniline, sodium salt, monohydrate) (Dojindo Laboratories; Kumamoto, Japan). The handle 4 and absorbent layer 2 were attached with an adhesive layer 3, which was FAS-TAPE 8311 double-coated acrylic-based adhesive (Avery-Dennison, Inc.; Pasadena, Calif.). These common features were modified in the three models as follows.

Model A, which featured the air gap, also had a translucent window 6 of MYLAR D 4 mil-thick transparent polyester film (Dupont & Co.; Wilmington, Del.). The film was treated by dipping in PERFECT VIEW non-aerosol anti-fog lens cleaner (Tyr Sport Inc.; Huntington Beach, Calif.). The film was attached to the handle 4 by an adhesive layer 5, which was the same as adhesive layer 3 above. A second layer 1 was T667 or 6664 spunbonded white polyester fabric (Reemay, Inc.; Old Hickory, Tenn.). The second layer was treated with between 0.0001% and 0.1% PLURONIC polyoxypropylene polyoxyethylene block copolymer (Pragmatics Inc.; Oak Ridge, Tenn.), 8% mannitol, and 0.15% hexadimethrin, all in a 0.85% NaCl solution.

Model B had a second layer 1 of hydrophillic 0.0635 cm thick POREX XM-1342 sintered high density polyethylene (HDPE) treated as described for second layer 1 in Model A. The layer was further treated as described in U.S. patent application Ser. No. 09/006,787, filed Jan. 14, 1998.

Model C had a second layer 1 of T667 or 6664 spunbonded white polyester fabric (Reemay, Inc.; Old Hickory, Tenn.). The second layer was treated as described for second layer 1 in Model A.

II. Preparation of Test Samples and Measurement Methods

Whole blood samples, treated with tripotassium ethylenediaminetetraacetate (EDTA) as an anticoagulant, were prepared by allowing the samples to metabolize to a value less than 50mg/dL, then spiking the sample with a concentrated glucose solution. The final glucose concentration of the sample was verified by a YSI Stat-2300 Glucose Analyzer (Yellow Springs Instruments Inc., Yellow Springs, Ohio).

The sample was then applied to a test strip when inserted into a device containing a reflectance meter. A light-emitting diode (LED) in the device directed light having a wavelength of 635 nm to the viewing surface of the absorbent layer 2b essentially along line of sight 7. The reflectance of the viewing surface 2b was measured by the reflectance meter over time using a silicon photodiode, which generated an analog signal. The signal was then processed by a transconductance amplifier, a synchronous detector, an analog-to-digital converter and a microprocessor. Automated processing and analysis of such detector signals is well known in the field of medical devices (see, for example, U.S. Pat. No. 5,597,532). The microprocessor then displayed the calculated values for the concentration of glucose based on a standard curve using samples having known glucose concentrations.

III. Improved Measurement Consistency From Using Air Gap

The following example shows that test strips featuring an air gap provide more consistent measurements than models without an air gap.

Blood samples with an adjusted hematocrit of 40% were prepared at five concentrations of glucose: about 50, 100, 200, 350 and 500 mg/dL. The concentrations were later verified by the YSI Stat-2300 Glucose Analyzer. Samples of 15 μL were applied to 16 strips of each of the three models and measured using the device described in Example II. The results were as follows in terms of the percent coefficient of variation (%CV=standard deviation/mean):

| Glucose mg/dL (by YSI) | Model A % CV | Model B % CV | Model C % CV |
|---|---|---|---|
| 60 | 2.1 | 3.6 | 4.3 |
| 106 | 2.9 | 3.2 | 2.2 |
| 197 | 4.0 | 10.3 | 4.2 |
| 351 | 2.3 | 6.6 | 6.6 |
| 520 | 3.8 | 7.4 | 9.8 |
| average%CV: | 3.0 | 6.2 | 5.4 |

These results show that Model A, which features the air gap, has a significantly less variability than Models B and C, which do not feature an air gap, resulting in more consistent measurements.

IV. Reduced Volume-dependency From Using Air Gap

As discussed above, the measured glucose concentration may vary, depending on the volume of the sample applied to the strip, because of wet-through. The following example shows that the measurements from test strips with an air gap are less subject to variation due to changes in the volume of the sample.

Blood samples were prepared at about 100, 300 and 500 mg/dL as described in Example III. Samples of 3.5, 4, 5, 10, 15, 20, 30 and 40 μL of each concentration were applied to 4 strips each of models A and B, and measured using the device described in Example II.

The results are shown in FIG. 4, which show the average measured glucose concentrations (y-axis) using models A (three sets of solid lines) and B (three sets of dotted lines) for varying sample volumes (x-axis) and varying actual glucose concentrations (upper, middle and lower pairs of solid and dotted lines). It is apparent that measured glucose concentrations for Model A, with the air gap, is more consistent across a range of sample volumes from 4 μl to 40 μl. In contrast, the measurements from Model B are only somewhat consistent between 10 μl and 40 μl.

This shows that the measured concentration using Model A, which has an air gap, is less likely than Model B to be affected by the volume of the sample.

V. Improved Hematocrit-independence From Using Air Gap

Measurements of glucose concentration can also vary depending on the hematocrit, which is a measure of the relative amounts of red blood cells and plasma in a blood sample. The following example shows that the results from test strips with an air gap are less likely to be affected by the hematocrit of the blood sample than test strips without an air gap.

Blood samples were prepared at about 100, 200 and 400 mg/dL as described in Example III with hematocrits of 0 (plasma), 20, 30, 40, 50, 60 and 80%, where 80% represents the hematocrit of a sample when it is spun at 5000 rpm for 30 minutes and all plasma is removed. Sample volumes of 15 μl were applied to each of 8 strips of Models A and B each, using the device described in Example II.

These results, as shown in FIG. 5, show the average measured glucose concentrations (y-axis) using models A (three sets of solid lines) and B (three sets of dotted lines) for varying sample hematocrit values (x-axis) and varying actual glucose concentrations (upper, middle and lower pairs of solid and dotted lines). It is apparent that Model A yields relatively consistent glucose measurements over the range of hematocrit values. In contrast, Model B can yield misleadingly low measurements as the hematocrit increases, especially when the sample contains high concentrations of glucose. Thus, the measurements using Model A, which features the air gap, are less hematocrit-dependent than Model B, which lacks an air gap.

Although the present invention has been described by the disclosed embodiments, those skilled in the art will readily appreciate that the specific examples are provided to illustrate, not to limit, the invention. It should be understood that various modifications can be made without departing from the spirit of the invention. Accordingly, the invention is limited only by the following claims.

We claim:

1. A method for controlling the absorption of a liquid sample through an absorbent layer, comprising the steps of;
   (a) providing an air gap defined by an absorbent layer, at least one side wall and a translucent window;
      wherein the air gap is a closed chamber containing ambient air pressure, and
      wherein the absorbent layer is permeable to gas when dry, but is relatively less permeable to gas when at least partially saturated with liquid;

(b) applying a liquid sample to the absorbent layer on the side opposite to the air gap such that the air pressure of the air gap is increased, thereby controlling liquid sample absorption by the absorbent layer.

2. The method of claim 1, wherein the sample is a human body fluid.

3. The method of claim 2, wherein the fluid is a blood sample.

4. An apparatus comprising an absorbent layer, at least one side wall and a translucent window, wherein the layer, at least one side wall and translucent window define an air gap, and wherein the air gap is a closed chamber containing ambient air pressure; and wherein the absorbent layer is permeable to gas when dry, but is relatively less permeable to gas when at least partially saturated with liquid; and wherein the absorbent layer, at least one sidewall, translucent window and air gap are adapted such that application of a liquid sample to the absorbent layer increases the air pressure of the air gap, thereby controlling liquid sample absorption by the absorbent layer.

5. The apparatus of claim 4, wherein the window is non-fogging.

6. The apparatus of claim 4, wherein the absorbent layer contains a reagent that indicates the presence of an analyte.

7. The apparatus of claim 4, further comprising a second layer in contact with the absorbent layer.

* * * * *